United States Patent [19]

Hijiya et al.

[11] Patent Number: 4,927,636

[45] Date of Patent: May 22, 1990

[54] ASSOCIATION COMPLEX COMPRISING PULLULAN AND POLYETHYLENE GLYCOL, AND PREPARATION AND USES OF THE SAME

[75] Inventors: Hiromi Hijiya; Toshio Miyake, both of Okayama, Japan

[73] Assignee: 501 Kabushiki Kaisha Hayashibara Kagaku Kenkyujo, Okayama, Japan

[21] Appl. No.: 116,329

[22] Filed: Nov. 3, 1987

[30] Foreign Application Priority Data

Nov. 11, 1986 [JP] Japan ................... 61-268305

[51] Int. Cl.$^5$ ................. A01N 25/34; A61K 9/26; A61K 47/00; C05G 5/06
[52] U.S. Cl. ................................ 424/409; 71/11; 71/27; 71/64.11; 424/49; 424/78; 424/418; 424/426; 424/443; 424/457; 424/468; 424/479; 424/481; 424/485; 424/486; 424/488; 424/499; 424/500; 424/501; 514/54; 514/777; 514/782; 514/947; 514/953; 514/963; 514/964; 514/965
[58] Field of Search ............... 424/489, 409, 418, 426, 424/443, 457, 468, 469, 479, 481, 485, 486, 488, 499, 500, 501, 49, 78, 150; 71/11, 27, 64.11; 514/54, 777, 782, 947, 953, 963, 964, 965

[56] References Cited

U.S. PATENT DOCUMENTS

| | | | |
|---|---|---|---|
| 3,962,155 | 6/1976 | Usamoto | 521/84.1 |
| 4,029,616 | 6/1977 | Nakashio et al. | 204/157.62 |
| 4,186,024 | 1/1980 | Fujimoto et al. | 106/162 |
| 4,618,664 | 10/1986 | Ohnishi | 527/315 |
| 4,650,666 | 3/1987 | Izutsu | 424/479 |
| 4,695,467 | 9/1987 | Uemura et al. | 424/489 |
| 4,764,360 | 8/1988 | Malson | 424/2 |

FOREIGN PATENT DOCUMENTS

| | | |
|---|---|---|
| 2264896 | 3/1974 | France . |
| 2314933 | 6/1975 | France . |
| 60-219238 | 11/1985 | Japan . |
| 61-112012 | 5/1986 | Japan . |
| 62-048618 | 3/1987 | Japan . |

*Primary Examiner*—Dennis Albrecht
*Assistant Examiner*—Ron Krasnow
*Attorney, Agent, or Firm*—Browdy & Neimark

[57] ABSTRACT

Pullulan forms an association complex with PEG in a hydrous system. The assocation complex, as well as its pullulan and PEG components, exerts a decreased solubility in water. The association reduces or even eliminates the excessively high water-solubility, threading and stickiness of pullulan so that this extends the uses of pullulan and PEG such as those in gradually disintegrable- and sustained release-shaped articles for consumer's products, toiletries, cosmetics, pharmaceuticals and feeds.

13 Claims, 3 Drawing Sheets

ASSOCIATION COMPLEX COMPRISING PULLULAN AND POLYETHYLENE GLYCOL, AND PREPARATION AND USES OF THE SAME

BACKGROUND OF THE INVENTION

1. Field of the Invention

The present invention relates to an association complex comprising pullulan and polyethylene glycol, and preparation and uses of the same.

More particularly, the present invention relates to an association complex comprising pullulan and polyethylene glycol wherein the pullulan and polyethylene glycol exert a decreased solubility in water.

Polyethylene glycol will hereinafter be abbreviated as "PEG", and the association complex with pullulan will be designated as "association complex".

2. Description of the prior art

Pullulan is a viscous glucan produced by culturing a microorganism of the species *Aureobasidium pullulans* on a nutrient culture medium containing saccharide(s) such as monosaccharide and lower oligosaccharide under aerobic conditions. Hayashibara Co., Ltd., Okayama, Japan, is the sole company that commercializes pullulan on an industrial scale.

Since pullulan has characteristic properties such as water-solubility, edibility, transparency, oil-resistance, gas-barrier property, gloss and adhesion, it has been extensively used as a base material for foods, beverages, cosmetics and pharmaceuticals, as well as to prepare various shaped articles, for example, granule, tablet, rod, film and sheet.

Recently, as in the case of shaped articles for pharmaceutical uses, gradually disintegrable shaped articles that are imparted with controlled solubility and disintegration rate in a hydrous system in order to retain their efficacy over a prescribed period, and also sustained release shaped articles that gradually release the effective ingredient have been in great demand.

Although shaped articles containing intact pullulan are characterized in that they smoothly dissolve and disintegrate in water, these properties render the preparation of gradually disintegrable- and sustained release-shaped articles with pullulan very difficult.

To improve this, the present inventors propose in Japanese Patent Laid-Open No. 219,237/85 a shaped article wherein a heteromannan is incorporated together with pullulan.

Such shaped article has the demerits that its preparation is relatively complicated, as well as that the solubility may be still too high, dependent on the use.

SUMMARY OF THE INVENTION

We investigated association complexes comprising pullulan and a water-soluble polymer in order to decrease much more the solubility of pullulan in water.

As the result, we found that when allowed pullulan to contact with water-soluble polymers in a hydrous system, unlike the other water-soluble polymers tested, PEG, commercialized by Nipp Oil & Fats Co., Ltd., Tokyo, Japan, under the trade name of "Macrogol", specifically forms an association complex wherein the water-solubilities of pullulan and PEG are extremely decreased, as well as that the association complex can be easily recovered.

DETAILED DESCRIPTION OF THE INVENTION

Figure 1:
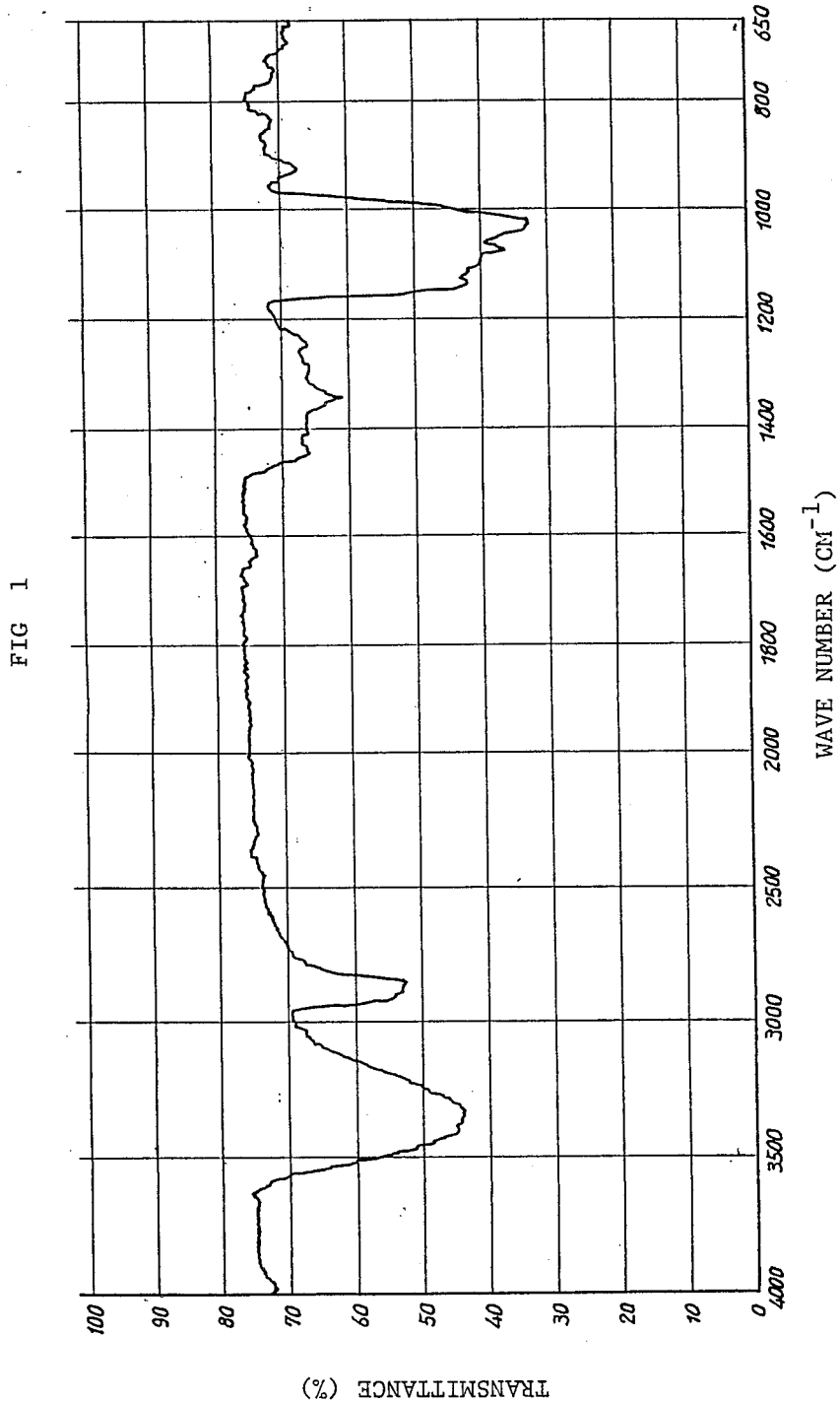
FIG. 1 is the infrared spectrum of the association complex.

Intrinsically, both pullulan and PEG are polymers that are readily soluble in water.

The solubility of the association complex per se is extremely low in water, and the pullulan and PEG exert a decreased solubility in water.

An appropriate amount of a powdered association complex gives a white suspension when added in test tube with water. The association complex is solubilized with a relative ease to release pullulan and PEG by dissolving a relatively large amount of salt or admixing thereto a hydrogen bond destroying agent such as dimethyl sulfoxide, formamide and urea. This suggests that in the association complex pullulan molecules and PEG molecules are strongly bound via hydrogen bonds and the bonds are responsible for the decrease in water-solubility.

Preparation of the association complex will hereinafter be explained.

The association complex is obtained by allowing pullulan to contact with PEG in a hydrous system, for example, in solution. For example, an aqueous pullulan solution and a liquid PEG are mixed, and the resultant association complex in a concentrate or white turbid form is recovered.

In this case, with respect to one part by weight of pullulan, generally, 0.01–100 parts by weight, preferably, 0.1–10 parts by weight of PEG, d.s.b., is used.

"d.s.b." is the abbreviation of dry solid basis.

Pullulan with a molecular weight in the range of 10,000–5,000,000 can be used in the invention, regardless of its preparation method.

Any PEG can be used in the invention, as long as it is in solution. For example, a liquid PEG with a relatively low molecular weight, for example, 200–600, is used intact or in aqueous solution, while a solid PEG with a relatively high molecular weight, for example, 1,000–10,000, is melted into liquid by heating or prepared into aqueous solution prior to its use.

The resultant association complex in concentrate or white turbid form can be easily recovered by decantation, filtration, and/or centrifugal separation.

The white gummy association complex thus obtained can be directly prepared into paste, or, if necessary, dried into powder or chips.

The association complex in an appropriate form, for example, solution, paste or powder, can be incorporated into the compositions and shaped articles of the invention during processings, for example, by adding, mixing, kneading, spraying, soaking, permeation or injection.

For example, an association complex formed in solution is prepared intact or in mixture with appropriate substance(s) into a liquid or paste composition, for example, cream, paste, ointment, poultice or feed.

In preparation of the association complex in solution, one or more appropriate substances can be advantageously incorporated in the association complex.

Furthermore, the association complex can be advantageously separated, recovered, if necessary, dried, pulverized and added with appropriate substance(s) to obtain a solid composition, for example, gradually disintegrable- or sustained release-shaped articles.

Examples of such substances include antibacterial agent, insecticide, coloring agent, flavoring agent, nutrient, bioactive substance, medicament, inclusion compound with cyclodextrin, plasticizer, filler, foaming agent, vehicle, and flame retarder.

The gradually disintegrable- or sustained release-shaped articles can be prepared into pulverulent, linear, plane or cubic shape, for example, granule, fiber, filament, rod, gauze, cloth, nonwoven fabric, film, sheet, paper, coating membrane, tube, capsule, tablet, sponge, or laminated article.

The compositions and shaped articles obtained in this way can be extensively used for or in consumers' products such as toiletries, cosmetics, pharmaceuticals including those for animal, and other orally-usable products, as well as for agriculture, fisheries, forestry, mining and manufacturing industries. In case of using the complex to prepare injections containing a bioactive substance such as interferon, tumor necrosis factor, interleukin, insulin, growth hormone and tissue plasminogen activator, advantageously the complex gradually releases the bioactive substance and prolongs its efficacy over a long time period when injected or placed intramuscularly or intraperitoneally.

The following Experiments will explain the association complex in detail.

EXPERIMENT 1

Behavior of water-soluble polymers in aqueous pullulan solution

Three milliliters aliquots of 30 w/v % aqueous solution of pullulan, average molecular weight of 200,000, were placed in test tubes, and to the aliquots was added 6 ml aliquot of 20 w/v % aqueous solution of either water-soluble polymer as listed in Table I.

Formation of association complex was checked by macroscopically observing the amount of the white insoluble form occurring with the decrease in water-solubility.

The results were as shown in Table I.

TABLE I

| Water-soluble polymer | White turbidity | Remarks |
|---|---|---|
| Polyvinyl alcohol | — | Control |
| PEG | +++ | Present invention |
| Sodium polyacrylate | — | Control |
| Polyvinyl pyrrolidone | — | Control |
| Carboxymethyl cellulose | — | Control |
| Dextran | — | Control |
| Gum arabic | — | Control |
| Pectin | — | Control |
| α-Cyclodextrin | — | Control |
| Maltotriitol | — | Control |

Note:
(+++) indicates that a large amount of white insoluble form occurs.

These data evidently show that, among the water-soluble polymers tested, pullulan forms an association complex specifically with PEG.

It was found that the association reduces the threading, adhesive and sticky properties which are the demerits of aqueous pullulan solution.

EXPERIMENT 2

Effect of molecular weight on the formation of the association complex

Pullulan and PEG were tested for the effect of molecular weight on the formation of the association complex.

Thirty w/v % aqueous solution of pullulan with one of the average molecular weights listed in Table II and 30 w/v % aqueous solution of PEG with one of the average molecular weights listed in Table II were mixed in accordance with the method in Experiment 1, and the formation of association complex was checked by macroscopically observing the amount of the resultant white insoluble form.

The results were as shown in Table II.

These data evidently show that the average molecular weight of PEG influences its association with pullulan, as well as that a PEG with an average molecular weight in the range of 200–10,000, preferably, 400–6,000, can be advantageously used in the association.

Also was found that the molecular weight of pullulan scarcely influences the association.

TABLE II

| | Pullulan | | | |
|---|---|---|---|---|
| PEG | 100,000 | 200,000 | 1,000,000 | Remarks |
| 200 | ++ | ++ | ++ | Present invention |
| 400 | +++ | +++ | +++ | Present invention |
| 1,200 | +++ | +++ | +++ | Present invention |
| 2,000 | +++ | +++ | +++ | Present invention |
| 6,000 | +++ | +++ | +++ | Present invention |
| 10,000 | ++ | ++ | ++ | Present invention |
| 15,000 | — | — | — | Control |
| 20,000 | — | — | — | Control |

EXPERIMENT 3

Physicochemical properties of the association complex

An aqueous solution of pullulan, average molecular weight of 200,000, and that of PEG, average molecular weight of 400, were mixed according to the method in Experiment 1, and the resultant association complex was recovered by filtration, washed with ethanol, dried and pulverized.

(1) A small portion of the association complex gives a white suspension when added in test tube with water. The association complex is readily solubilized to release pullulan and PEG by heating or adding thereto a relatively large amount of salt or a hydrogen bond destroying agent such as dimethyl sulfoxide, formamide or urea.

(2) Carbonization point

The association complex in powder undergoes carbonization and degradation at 200±20° C. when heated.

(3) Ultraviolet absorption spectrum

No characteristic absorption is observed.

(4) Infrared absorption spectrum

Figure 2:
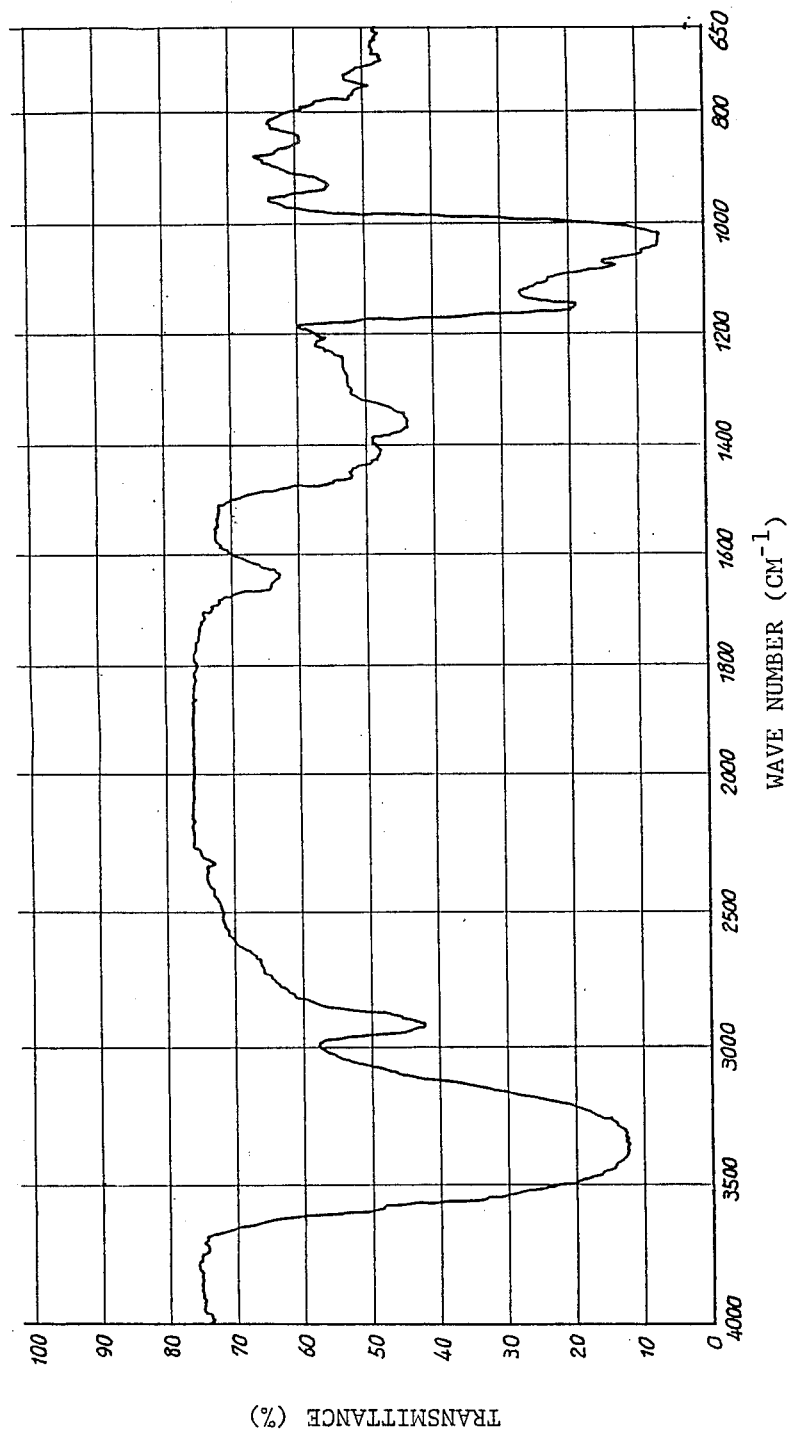
FIG. 2 is the infrared spectrum of pullulan as control.
Figure 3:
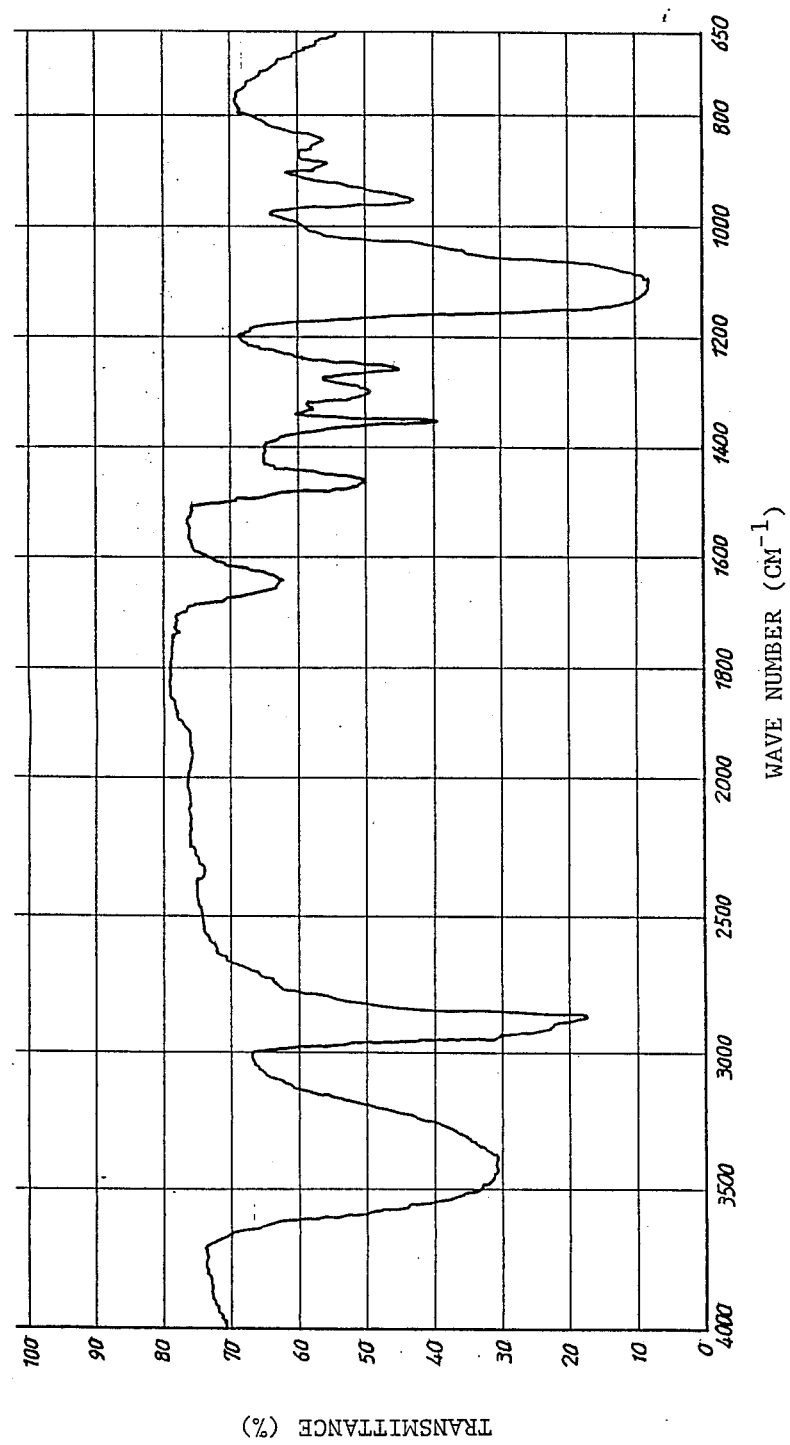
FIG. 3 is the infrared spectrum of PEG as control.

Infrared absorption spectrum was determined by the film method. The results were as shown in FIG. 1. As control, the infrared absorption spectra of pullulan and PEG are given respectively in FIGS. 2 and 3.

(5) Solubility in solvents

Gradually dissoluble in cold water. Soluble in hot water, dimethyl sulfoxide and formamide. Scarcely soluble in methanol and ethanol. Insoluble in ethyl ether and petroleum benzine.

(6) Coloring reaction

Anthrone-sulfuric acid reaction, turned green; ninhydrin reaction, negative; and iodine reaction, turned yellowish brown or greenish brown.

(7) Behavior in solution

A solution in hot water is neutral or slightly acidic.

(8) Appearance

White or pale yellow powder.

As evident from the above data, the association complex of the invention is a novel composition entirely different from the material pullulan and PEG.

Several embodiments will explain the preparation and uses of the association complex.

EXAMPLE 1

Powder

Ten liters of 30 w/v % aqueous solution of pullulan, average molecular weight of 200,000, was added with 3 liters of PEG, average molecular weight of 400, and the resultant white insoluble form was recovered by removing the supernatant by decantation, dried and pulverized to obtain about 4.5 kg of a white powder.

Since the product dissolves in water much more slowly than that prepared solely with pullulan, it can be advantageously used in gradually disintegrable- and sustained release-shaped articles.

EXAMPLE 2

Film

Twenty liters of 15 w/v % aqueous solution of pullulan, average molecular weight of 800,000, was added with 2 kg of PEG, average molecular weight of 4,000, while heating, and the resultant mixture solution was casted on 60° C. chromium coated metal roll. The resultant 0.03 mm thick film was taken off at a rate of 3 meters/minute, and then dried in 90° C. air stream.

The product is a white and semitransparent film containing an association complex of the invention that, unlike pullulan film, did not readily dissolve but gradually disintegrated in a hydrous system.

EXAMPLE 3

Tablet

Six parts by weight of an association complex in powder, obtained by the method in Example 1, was added with 2 parts by weight of a powdered zinc, and the resultant mixture was prepared with 20 R punch, 12 mm in diameter, into 5.25 mm thick tablets.

Since the tablets gradually dissolve and disintegrate without causing a drastic reaction to generate a constant level of hydrogen gas when placed in dilute sulfuric acid, hydrogen gas can be safely generated with the tablets.

EXAMPLE 4

Fertilizer rod

A composition fertilizer comprising 14% of nitrogen, 8% of $P_2O_5$ and 12% of $K_2O$ was added homogeneously with 14 parts by weight of an association complex in powder obtained by the method in Example 1, 5 parts by weight of calcium sulfate and 1 part by weight of water, and the resultant mixture was prepared into rods by heating it to 80° C. with an extruder, L/D of 20, compression ratio of 1.8, equipped with 30 mm die.

The product is easily handleable and does not necessarily require special packaging. The mechanical strength of the product is sufficient for deep placement.

Since after manuring the product gradually dissolves and disintegrates, it is a suitable sustained release fertilizer.

EXAMPLE 5

Dentifrice

A dentifrice was prepared by mixing 45.0 w/w % of calcium monohydrogen phosphate, 2.75 w/w % of pullulan (average molecular weight of 400,000), 3.0 w/w % of PEG (average molecular weight of 1,500), 1.5 w/w % of sodium lauryl sulfate, 17.0 w/w % of glycerine, 0.5 w/w % of polyoxyethylene sorbitan monolaurate, 0.05 w/w % of antiseptic, 0.2 w/w % of α-G Sweet, an α-glycosyl stevioside commercialized by Toyo Sugar Refining Co., Ltd., Tokyo, Japan, and 30.0 w/w % of water.

The product with a moderate sweetness is a suitable dentifrice for children.

The product containing an association complex of the invention is an easily handleable dentifrice that is much lower in threading and stickiness than that prepared solely with pullulan.

EXAMPLE 6

Ointment

Six hundred grams of pullulan, average molecular weight of 200,000, and 6.5 kg of maltose were dissolved in 3 liters of water by heating, and the resultant mixture was added with 1.2 liters of Macrogol 400 (average molecular weight of 400) containing 20 g of iodine. The resultant was bottled to obtain the captioned product.

The product, containing iodine and maltose respectively as disinfectant and nutrient, can be advantageously used as an ointment to treat external wounds such as abrasion, incisure and burn.

The product containing an association complex of the invention is an easily applicable ointment that is much lower in threading, stickiness and superficial slippiness than that prepared solely with pullulan.

As obvious from the above, the association complex of the invention lowers the solubility of pullulan and PEG in water, and this reduces their excessively high solubility in a hydrous system.

The present invention reduces the threading and stickiness of pullulan.

Incorporation of the association complex facilitates preparation of gradually disintegrable- and sustained release-shaped articles, as well as facilitating preparation of cream and ointment that are free of stickiness and superficial slippiness.

The association complex of the invention will extend the use of pullulan and PEG.

Having described specific embodiments of our bearing, it is believed obvious that modifications and variations of our invention are possible in light of the above teaching.

We claim:

1. A complex, comprising pullulan and polyethylene glycol associated on a molecular level via hydrogen bonds and having a decreased water solubility with respect to the water solubility of said pullulan and said polyethylene glycol, said polyethylene glycol having a molecular weight in the range of about 200–10,000, and wherein the amount of polyethylene glycol is in the range of 0.01–100 parts by weight with respect to one part by weight of pullulan, based on the dry solid.

2. The complex of claim 1 wherein the amount of polyethylene glycol is in the range of 0.1–10 parts by weight with respect to one part by weight of pollulan.

3. A process for preparing a complex comprising pullulan and polyethylene glycol associated on a molecular level via hydrogen bonds and having a decreased water-solubility with respect to pullulan and the polyethylene glycol, said process comprising:

contacting pullulan with the polyethylene glycol in a hydrous system to effect association wherein the amount of the polyethylene glycol is in the range of 0.01–100 parts by weight with respect to one part by weight of pullulan, based on the dry solid, and the molecular weight of the polyethylene glycol is in the range of about 200–10,000; and recovering the resultant complex.

4. The product of the process of claim 3.

5. A process according to claim 3 wherein the amount of polyethylene glycol is in the range of 0.1–10 parts by weight with respect to one part by weight of pullulan.

6. A process for preparing a composition, said process comprising the step of mixing (1) a complex comprising pullulan and polyethylene glycol associated on a molecular level via hydrogen bonds and having decreased water-solubility with respect to pullulan and said polyethylene glycol wherein the amount of the polyethylene glycol is in the range of 0.01–100 parts by weight with respect to one part by weight of pullulan, based on the dry solid, and the molecular weight of the polyethylene glycol is in the range of about 200–10,000, and (2) at least one additional substance selected from the the following an antibacterial agent, an insecticide, a coloring agent, a flavoring agent, a nutrient, a bioactive substance, a medicament, an inclusion compound with cyclodextrin, a plasticizer, a filler, a foaming agent, a vehicle and a flame retarder.

7. The process of claim 6, wherein said complex is obtained by contacting pullulan with polyethylene glycol in a hydrous system to effect association.

8. The process of claim 6, wherein said composition is a paste.

9. The process of claim 6, wherein said composition is a gradually disintegrable- or a sustained release-composition.

10. The process of claim 6, wherein said composition is toiletry, cosmetic or a pharmaceutical.

11. A process in accordance with claim 6 where the amount of polyethylene glycol is in the range of 0.1–10 parts by weight with respect to one part by weight of pullulan.

12. The product of the process of claim 6.

13. The product of claim 12 in the form of a gradually disintegrable- or sustained release-shaped product.

* * * * *